[19] United States Patent
Lewis et al.

[11] Patent Number: 5,513,956
[45] Date of Patent: May 7, 1996

[54] CIRCULATORY ASSISTED DEVICE WITH MOTOR DRIVEN GAS PUMP

[75] Inventors: Jeffrey P. Lewis, Wyomissing; Daniel J. Frank, Reading; Ray K. Newswanger, Terre Hill, all of Pa.

[73] Assignee: Arrow International Investment Corp.

[21] Appl. No.: 182,407

[22] Filed: Jan. 14, 1994

[51] Int. Cl.$^6$ .................................................. F04B 49/00
[52] U.S. Cl. .......................... 417/12; 471/315; 471/415; 471/395; 471/413.1; 623/3
[58] Field of Search ................ 417/12, 315, 413.01, 417/415, 395; 623/3 X

[56] References Cited

U.S. PATENT DOCUMENTS

| | | |
|---|---|---|
| 3,266,487 | 8/1966 | Watkins et al. . |
| 3,572,979 | 3/1971 | Morton ........................... 417/427 |
| 3,610,782 | 10/1971 | McGuire, III ..................... 417/326 |
| 3,720,199 | 3/1973 | Rishton et al. . |
| 3,720,200 | 3/1973 | Laird . |
| 3,769,960 | 11/1973 | Robinson . |
| 4,074,586 | 2/1978 | Nussbaum ........................ 74/424.8 |
| 4,272,225 | 6/1981 | Fujunaka et al. .................... 417/417 |
| 4,332,254 | 6/1982 | Lundquist . |
| 4,439,186 | 3/1984 | Kuhl . |
| 4,771,765 | 9/1988 | Choy et al. . |
| 4,794,910 | 1/1989 | Mushika . |
| 4,822,357 | 4/1989 | Forster et al. ....................... 623/3 |
| 4,832,005 | 5/1989 | Takamiya et al. . |
| 5,006,104 | 4/1991 | Smith et al. ....................... 600/16 |
| 5,152,776 | 10/1992 | Pinchuk . |
| 5,158,529 | 10/1992 | Kanai . |
| 5,169,379 | 12/1992 | Freed et al. . |
| 5,173,015 | 12/1992 | Maynard .......................... 408/137 |
| 5,186,615 | 2/1993 | Karliner ........................... 417/387 |
| 5,282,850 | 2/1994 | Davidson .......................... 623/3 |

FOREIGN PATENT DOCUMENTS

| | | |
|---|---|---|
| 0297723 | 4/1989 | European Pat. Off. . |
| 7900309 | 11/1980 | WIPO . |

Primary Examiner—Richard A. Berisch
Assistant Examiner—Xuan M. Thai
Attorney, Agent, or Firm—Amster, Rothstein & Ebenstein

[57] ABSTRACT

A balloon pump for a circulatory assist device, the pump comprising a pumping chamber of variable volume in which a diaphragm assembly is displaceable in first and second pumping directions to inflate and deflate the balloon, the diaphragm assembly comprising a diaphragm sandwiched between a pusher plate and a retainer plate where the pusher plate and retainer plate are affixed to an elongated shaft having an external threaded portion disposed in a planetary roller nut, a rotor assembly is affixed to the roller nut and a stator assembly is disposed outwardly of the rotor assembly to impart bidirectional rotation to the roller nut to cause the shaft and diaphragm assembly to move in the first and second pumping directions, the pump communicating with a pump control unit and microprocessor for controlling pump operation.

5 Claims, 4 Drawing Sheets

CIRCULATORY ASSISTED DEVICE WITH MOTOR DRIVEN GAS PUMP

BACKGROUND

The present invention relates generally to circulatory assist devices for the heart, and more particularly, to a pump having a high-speed, motor-driven actuator.

Circulatory assist procedures such as intra-aortic balloon counterpulsation increase coronary profusion and decrease myocardial oxygen consumption. During the normal cardiac cycle, the atrium first contracts (atrial systole) and the ventricles fill with blood through the atrioventricular valves. The ventricles then contract (ventricular systole) in response to an electrical impulse. Immediately after ventricular contraction starts, ventricular pressure rises abruptly causing the atrioventricular valves to close. The volume of blood within the ventricles just prior to the closure of the atrioventricular valves is known as ventricular preload. As the ventricles continue to contract, blood pressure in the ventricles continues to rise. These are known as isovolumetric contractions since muscular contraction occurs without a change in volume, and This portion of the cardial cycle results in a majority of myocardial oxygen consumption. The resistance in the arterial circulation against which the ventricle muscles must pump and the resultant left ventricular wall tension during systole is called afterload. When the pressure in the ventricles exceeds the pressure in the circulation, blood flows from the left ventricle into the aorta via the aortic valve, and from the right ventricle into the pulmonary artery via the pulmonic valve. At the termination of ventricular ejection, the ventricles relax. When the blood pressure within the ventricles drops below the systemic pressure, the aortic and pulmonic valves close signifying the onset of isovolumetric relaxation (ventricular diastole). When the ventricular pressure drops below the pressure in the atria, the atrioventricular valves open and the cycle starts again as the ventricles fill with blood.

Myocardial oxygen consumption is dependent upon heart rate, afterload, preload and contractility. When the myocardium is injured, the patient's heart action is insufficient to meet myocardial demand. With cardiac failure, the myocardial oxygen supply is reduced. The circulatory system compensates by increasing preload, afterload and heart rate. This in turn further increases myocardial demand and a deteriorating cycle develops where myocardial oxygen supply continues to decrease while demand continues to increase.

The intra-aortic balloon is used to assist the weakened heart. The balloon catheter is percutaneously or surgically inserted into the patient's aorta to inflate and deflate in conjunction with the cardiac cycle. In this connection, it helps circulation by increasing aortic pressure during diastole to augment coronary profusion, and it decreases aortic pressure during systole to lower muscular demands on the left ventricle.

During diastole, when the left ventricle is relaxed and the coronary arteries are filling with oxygenated blood, the balloon is timed to inflate. This increases the coronary circulation and is known as diastolic augmentation or increasing the diastolic pressure.

When the left ventricle contracts to pump blood into the aorta, the balloon is deflated to decrease the pressure against which the left ventricle has to function, thereby reducing the afterload, and aortic end—diastolic pressure and systolic pressure. Through a combination of diastolic augmentation and a reduction in aortic end—diastolic pressure, afterload decreases, cardiac output increases, and blood circulation through the coronary vessels increases.

There are many circulatory assist devices known in the art. However, most are dependent upon a complex arrangement of compressors and vacuum pumps which operate in conjunction with pressure and vacuum accumulators to inflate and deflate the balloon. Examples are disclosed in U.S. Pat. Nos. 3,769,960 to Robinson, 4,794,910 to Mushika, 4,832,005 to Takamiya et al., 5,158,529 to Kanai and 5,169,379 to Freed et al.

To inflate the balloon, compressed gas stored in a pressure accumulator is typically applied to one side (the drive side) of a diaphragm or safety chamber causing it to displace gas (e.g., helium) on the other side (the balloon side). The displaced helium enters the balloon and causes it to inflate. To deflate the balloon, a vacuum is then applied to the drive side. The diaphragm separates high-pressure drive gas from the relatively low balloon pressure (usually less than 50 millimeters of Hg). Most pumps limit the drive gas to 300 millimeters Hg for safety reasons so that in the event of a diaphragm rupture, the balloon will not be exposed to pressures any higher than the drive pressure. This limitation on drive pressure limits the speed with which balloons can be inflated.

The present invention is directed to overcoming the disadvantages inherent in the prior art by providing a balloon pump having a motor-driven diaphragm assembly in lieu of the standard pneumatic arrangement. Mechanical diaphragm displacement reduces the number and size of the individual drive components, eliminates high pressure drive gas and required systems for evacuating the same in the event of a diaphragm rupture, and permits better system response. A pump in accordance with the present invention is equally suited for use in a ventricular assist device and the background and detailed description with regard to intra-aortic balloon catheters is not meant to be limiting.

SUMMARY OF THE INVENTION

In accordance with the present invention, there is provided a balloon pump for inflating and deflating a balloon in a circulatory assist device. The pump principally comprises a pump housing having an internally disposed pumping chamber of variable volume, a diaphragm assembly for varying the volume of the pumping chamber, and a motor-driven actuator for mechanically displacing the diaphragm assembly in a first pumping direction to decrease the volume of the pumping chamber to inflate the balloon, and in a second pumping direction to increase the volume of the pumping chamber to deflate the balloon.

The diaphragm assembly is comprised of a flexible diaphragm sandwiched between a pusher plate and a retainer plate. The diaphragm assembly is affixed to an elongated shaft having a threaded exterior portion to function as a planetary roller screw. The shaft is disposed within a planetary roller nut which is rotatably supported within the pump housing. A rotor assembly is affixed to the planetary roller nut and a stator assembly is disposed outboard of the rotor assembly within the pump housing to impart rotation to the planetary roller nut in a first direction such that the diaphragm assembly is displaced in the first pumping direction, and then a second direction such that the diaphragm assembly is displaced in the second pumping direction.

The balloon pump communicates with a pump motor controller and microprocessor for controlling all aspects of the pump operation. The microprocessor can be programmed with a plurality of pump positions for the diaphragm assembly where the last pump position corresponds to a fully inflated balloon (the assist-inflate position) and the initial diaphragm position corresponds to a fully deflated balloon (the assist-deflate position), the assist-deflate position being selectable by the microprocessor depending upon parameters such as balloon volume and catheter volume, and the stroke length being variable between the assist-deflate position and assist-inflate position to provide partial inflation.

The pump is pneumatically connected to a series of valves and tanks, controlled by a microprocessor, for priming the system with gas.

In accordance with the present invention, it is an object thereof to provide a balloon pump which utilizes a high-speed, motor-driven actuator to displace a diaphragm assembly in a pumping chamber of variable volume to inflate and deflate a balloon in a circulatory assist device.

It is another object of the present invention to provide a balloon pump which eliminates the need to drive a diaphragm with high-pressure drive gas through a multiplicity of valves and accumulator tanks for reduced system complexity.

It is yet another object of the invention to provide a balloon pump with superior system response by mechanically displacing a diaphragm assembly with a motor-driven actuator.

It still another object of the invention to provide a microprocessor-controlled balloon pump, in which a diaphragm assembly is displaceable between a plurality of preprogrammed pump positions between an assist-deflate position and an assist-inflate position where the stroke of the diaphragm assembly is variable to control the degree of balloon inflation.

In accordance with these and other objects which will become apparent hereinafter, the present invention will now be described with particular reference to the accompanying drawings.

DETAILED DESCRIPTION OF THE PREFERRED EMBODIMENT

Figure 1:
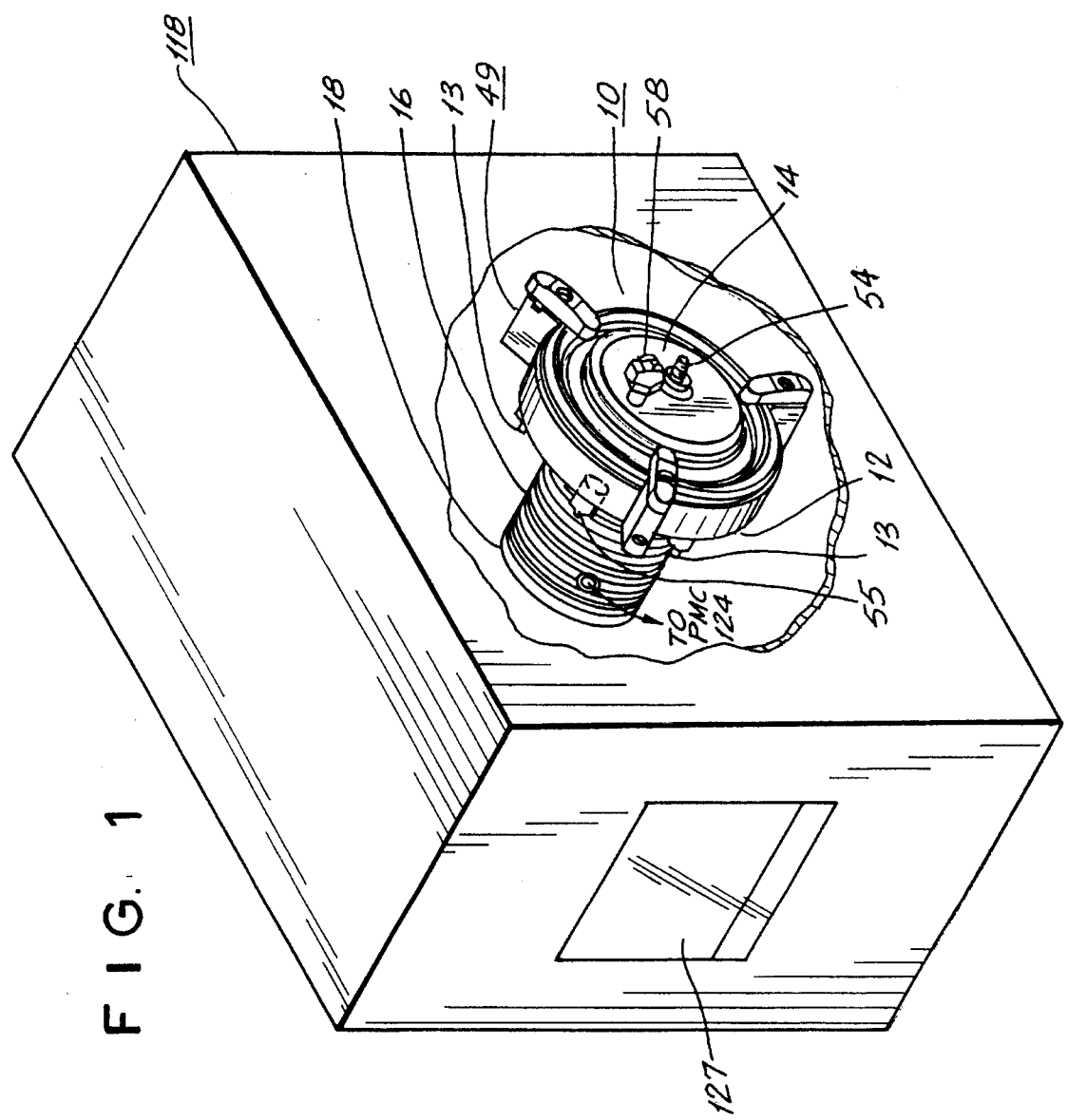
FIG. 1 is an isometric view of a pump disposed in a circulatory assist device.

With reference to the several views of the drawings, there is depicted a balloon pump generally denoted by the reference numeral 10 for use in a circulatory assist device 118.

Figure 2:
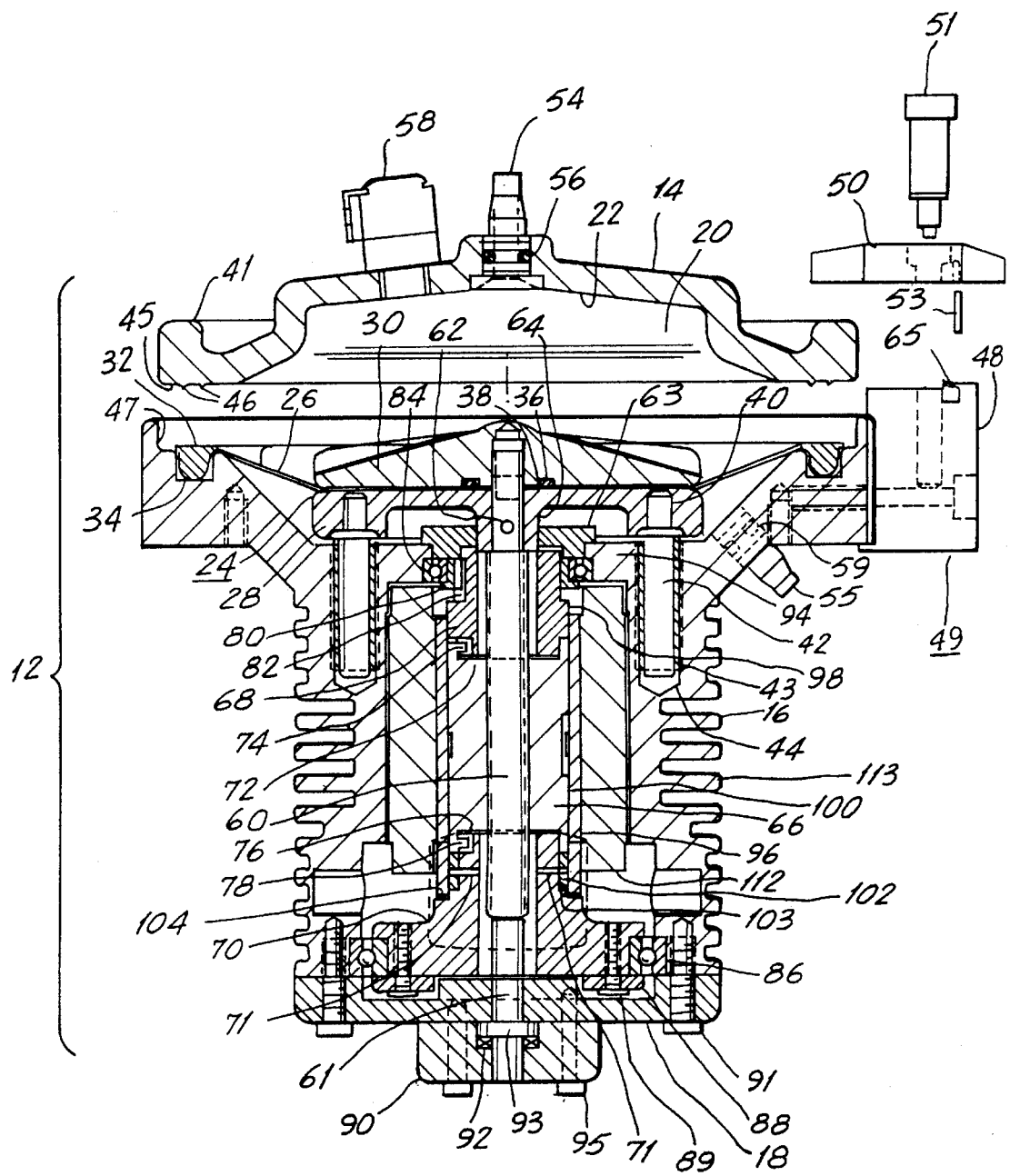
FIG. 2 is a sectional view of the pump depicting the diaphragm and actuator assembly.

Referring now to FIGS. 1 and 2, pump 10 has a pump housing assembly 12 primarily comprised of a removable front cover 14, a body portion 16, and a rear cover 18. The pump housing assembly 12 includes a plurality of pins 13 disposed in body portion 16 and extending rearwardly therefrom for mounting the pump within circulatory assist device 118. Housing assembly 12 includes an internally disposed pumping chamber 20 defined on one side by the inner surface 22 of front cover 14, and on the opposing side by a displaceable diaphragm assembly 24 for varying the volume of the pumping chamber.

Diaphragm assembly 24 is comprised of a flexible diaphragm 26 sandwiched between a pusher plate 28 and a retainer plate 30. Diaphragm 26 has a peripheral lip 32 which is recessed within a continuous slot 34 defined in body portion 16 to provide an outer seal with the housing when front cover 14 is clamped to body portion 16. An 0-ring 36 is disposed within a slot 38 in retainer plate 30 and against diaphragm 26 to form an inner seal. Pusher plate 28 defines a plurality of circumferentially disposed slots or apertures 40 which receive a corresponding number of guide pins 42. Guide pins 42 are slidably recessed within bushings 43 disposed in respective slots or apertures 44 defined in body portion 16 to resist rotation and maintain the alignment of pusher plate 28 and retainer plate 30 as they reciprocate during pumping.

Front cover 14 includes a rim 41 which fits within an annular shoulder 47 in body portion 16. A confronting surface 45 in front cover 14 contains surface undulations 46 which pinch lip 32 of diaphragm 26 to ensure pumping chamber 20 is properly sealed from the ambient. A plurality of clamp assemblies 49 are affixed to body portion 16 for clamping front cover 14 thereto. Each clamp assembly 49 consists of a clamp mounting block 48 attached to body portion 16, and a clamp latch 50 pivotal about pin 51 between open and clamping positions which overlaps rim 40 when oriented in the clamping position. A stop-pin 53 is affixed to latch 50 and limits the rotation thereof when rotated into the clamped position by engaging recess 65 in mounting block 48.

Figure 5:
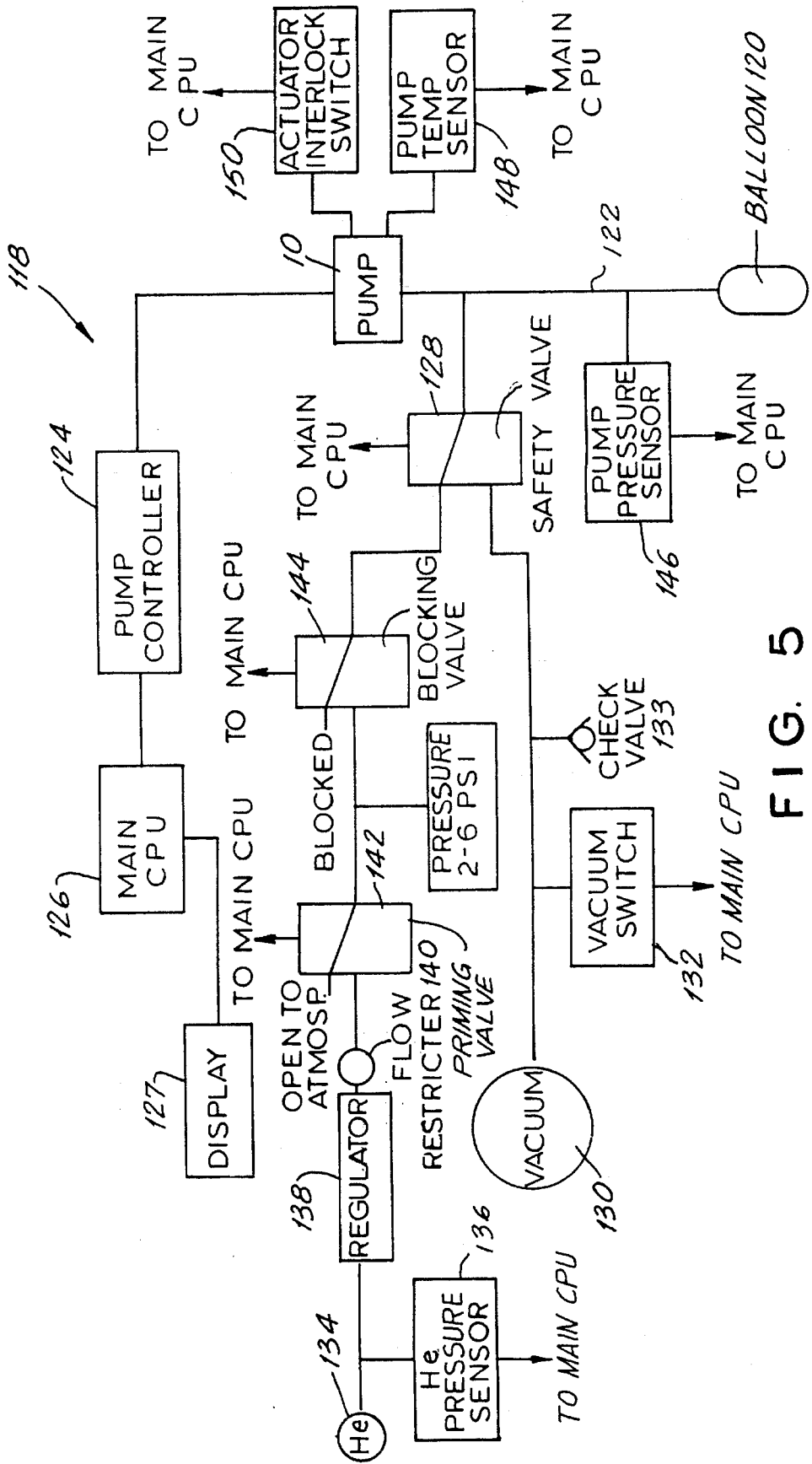
FIG. 5 is a block diagram of the circulatory assist device.

A centrally-positioned barb fitting 54 or the like is sealed with an O-ring 56 in front cover 14 to provide a means for fluidly communicating between pumping chamber 20 and the balloon catheter (identified schematically by the reference numeral 122, see FIG. 5). Disposed opposite pumping chamber 20 behind diaphragm 26, a second barb fitting 55 is sealed with an O-ring 59 in body portion 16. Fitting 55 is connected to a vent line (not shown) for evacuating air behind diaphragm 26 which would otherwise interfere with normal pump operation. A quick disconnect fitting 58 in front cover 14 serves as an intake port through which the system is primed with gas (e.g., helium) for the ballooning procedure as explained in greater detail hereinbelow.

As a means for mechanically displacing diaphragm assembly 24, an elongated shaft 60 extends axially within housing 12 through dust cover 63 and abuts a stop-pin 61. When shaft 60 is in contact with stop-pin 61, diaphragm assembly 24 is in the home position. Retainer plate 30 is threadably attached to shaft 60, and pusher plate 28 is affixed to shaft 60 by a pin 62 extending through the hub portion 64 of pusher plate 28. Shaft 60 includes an external thread which mates with a planetary roller nut 66. Planetary roller nut 66 is rotatably supported within body portion 16 of housing 12 by a front bearing hub 68 and a rear bearing hub 70. Front bearing hub 68 includes a keyway 72 in which a front roller nut key 74 is disposed. Similarly, rear bearing hub 70 includes a keyway 76 in which a rear roller nut key 78 is disposed. A key ring 80 is keyed to the front bearing hub 68 in keyway 82 thereof to provide a floating bearing assembly with front bearing 84 for radial support. Rear bearing hub 70 is supported within body portion 16 by rear bearing 86 for reacting axial and radial loads. Bearing 86 is clamped to rear bearing hub 70 by a retaining ring 88 with a plurality of circumferentially disposed fasteners 89. A sleeve 103 is attached to rear bearing hub 70 with pins 71. Rear cover 18 is fastened to body portion 16 with fasteners 91 and defines a centrally located aperture through which stop pin 61 passes into a retainer member 90. Retainer member 90 is attached to the rear cover 18 with fasteners 95 and defines an internal cavity in which a compression spring 92 abuts flange 93 of stop-pin 61 to cushion the rearward stroke of diaphragm assembly 24 such that pusher plate 28 does not slam into wall 94 of body portion 16 when the pump is homed.

Figure 3:
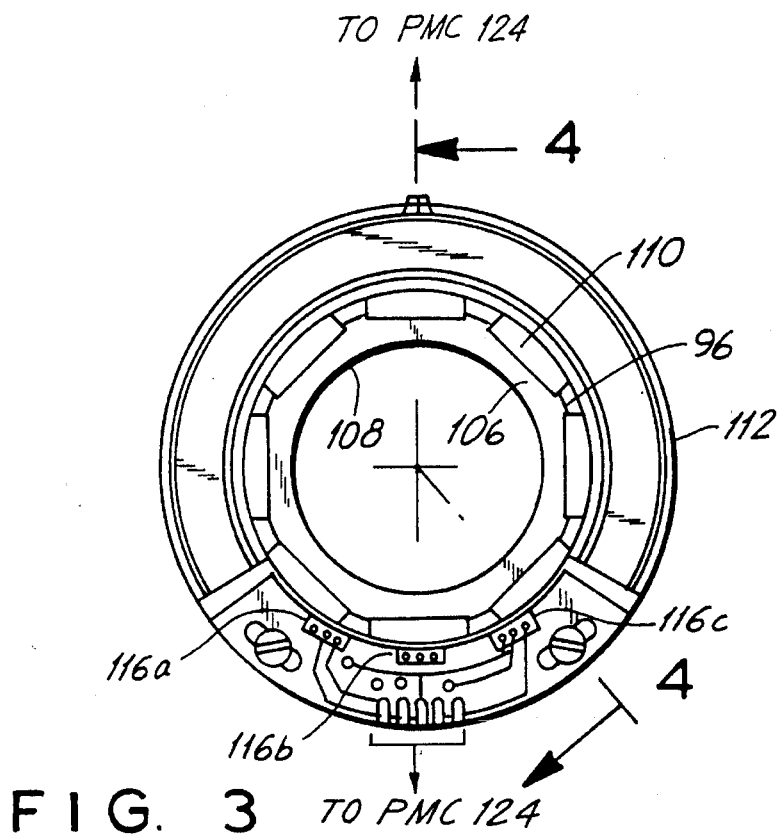
FIG. 3 is a top plan view of a rotor and stator assembly which form the motor for the actuator.
Figure 4:
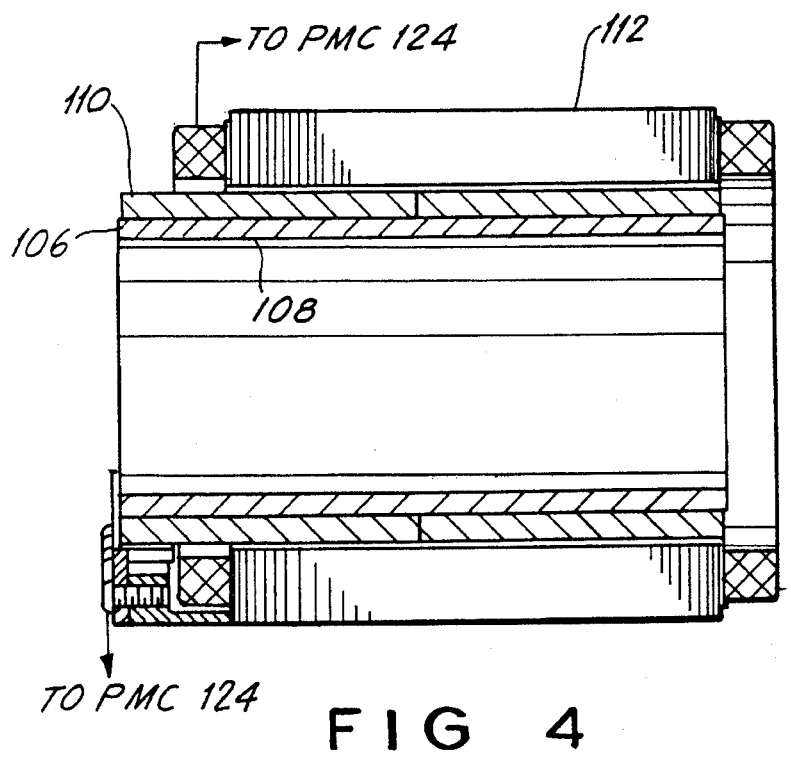
FIG. 4 is a sectional view along lines 4—4 in FIG. 3, showing the rotor assembly positioned within the stator assembly prior to installation in the pump housing.

Referring now to FIGS. 2, 3 and 4, as a means for translating shaft 60, an exemplary DC brushless motor comprises a rotor assembly 96 affixed to the exterior surface 98 of front bearing hub 68, the exterior surface 100 of planetary roller nut 66, and the exterior surface 102 of sleeve 103 and against annular shoulder 104 of rear bearing hub 70. Rotor assembly 96 comprises a cylindrical support member 106 having a hollow bore therethrough and an interior surface 108 which is bonded to respective exterior surfaces 98, 100 and 102 of front bearing hub 68, planetary roller nut 66 and sleeve 103, respectively. A plurality of permanent magnets 110 are attached to support member 106 by conventional methods. Alternatively, the rotor can be constructed from a single piece of magnetizable material having portions thereof magnetized in accordance with techniques well known in the art of electric motors.

A stator assembly 112 is disposed radially outwards of rotor assembly 96 from the shaft center line. In the preferred embodiment, a three-phase, donut-shaped stator assembly 112 includes three coils which are energized by signals from pump motor controller (PMC) 124 in response to sensor outputs from sensors 116*a*, 116*b* and 116*c* for commutation in a conventional manner. Stator 112 is affixed to the interior of body portion 16 by bonding or the like. Pump cooling is provided by a plurality of cooling fins 113 in body portion 16 to facilitate heat dissipation. The motor parameters are selected so as to drive diaphragm assembly 24 through the requisite stroke length between the corresponding fully deflated balloon position and the fully inflated balloon position within a time period on the order of less than 100 ms. The motor should be capable of developing a peak torque on the order of 150 oz-in.

Referring now to FIG. 5, a block diagram is illustrated of a circulatory assist device 118 for an intra-aortic balloon catheter. Pump 10 is connected to a balloon 120 through a catheter 122 (shown schematically). Pump 10 receives signals from PMC 124 which in turn communicates with a main CPU 126. The main CPU 126 is connected to a display 127 for showing various waveforms, statistics, user menus, user messages and alarms. The CPU 126 reads digitized waveform data such as ECG, auxiliary pressure, arterial pressure, QRS (ECG input with a band-pass filter) and balloon pressure. A trigger signal for timing inflation and deflation can be selected from an ECG, AV pacer, V pacer, direct pacemaker, arterial pressure or internal rate (an artificial trigger at a constant pace selected by the operator). The trigger point is not the exact moment of inflation, but rather the temporal reference point after which there is a delay until balloon inflation or deflation. As explained in the Background of the invention and as is well known, the balloon is timed to inflate at the dichrotic notch, the point on an arterial pressure tracing where a brief pressure drop and then rise within the aorta occurs after the systole as a result of the abrupt closure of the aortic valve signifying the onset of ventricular diastole. The inflate delay, time for initiation of balloon inflation, can be made adjustable, for example, between 0 to 225 ms, for a pressure trigger source (e.g., arterial pressure) and 50 to 500 ms for all other trigger sources (e.g., ECG), by a sliding potentiometer adjustable by the user. The deflate time is moment when the balloon is timed to deflate and can be set as a percentage of the current trigger to trigger detection interval. As an example, when the time between triggers is 1 second and the duration is set to 80%, then the balloon will be timed to deflate 800 ms after a trigger point (80% of 1 second). An exemplary input range is 40%–80% when pressure is selected as the trigger source and 60%–120% for all other trigger sources. The main CPU 126 can be programmed to determine the trigger to trigger duration using the current ECG rate or the length of the last heartbeat, whichever is less. If, for example, the ECG rate is 60 BPM and the last heartbeat took 2 seconds, the trigger duration will be calculated as 1 second. If the ECG rate is 60 BPM and the last heartbeat was 0.5 second, the trigger duration will be considered 0.5 second. If the deflate time is set to greater than 100% of the trigger to trigger time, the deflate time for the next inflation is calculated as 120% of the previous trigger to trigger interval. When the next trigger occurs, the deflate time is recalculated based on the actual trigger to trigger interval for that inflation. Thus, for example, if the triggers occur at a consistent 60 BPM for a trigger interval of 1 second, and the deflate time is 110%, when a trigger occurs, the deflate time for the next inflation is calculated as 120% of 1 second or 1.2 seconds. When the next trigger occurs 1 second later, the deflate time is recalculated as 1.1 seconds and the balloon deflates 0.1 second later.

Pump 10 displaces a volume of gas corresponding to the volume of balloon 120 and catheter 122. The initial position for the diaphragm assembly 24 (the assist-deflate position) is selected such that the volume of gas to be compressed in pumping chamber 20 (i.e., the preload volume) is equal to the volume of gas in catheter 122 and the volume of the balloon 120. The main CPU 126 can be programmed to provide pump 10 with an assist-deflate position for diaphragm assembly 24 upon receiving a set preload volume and balloon size from the user, and the degree of balloon inflation would be dependent upon displacement from that point. The diaphragm assembly 24 can be displaced through a given stroke length corresponding to a plurality of pump positions. If, for example, there are 91 possible pump positions numbered 6 through 96 programmed into the system and the preload volume for a particular application corresponds to pump position 16, a full stroke (100%) would be realized by moving diaphragm assembly 24 from pump position 16 (the assist-deflate position) to pump position 96 (the assist-inflate position). If a 50% stroke is selected (partial inflation), the diaphragm assembly 24 would move to pump position 57. The degree of balloon inflation can be controlled by the user who can increase or decrease the stroke length as required.

Pump 10 is pneumatically connected to a safety valve 128. Safety valve 128 is controlled by main CPU 126 and can be switched between a vacuum source and a priming source for charging the system with Helium. The vacuum is stored in a vacuum accumulator tank 130 and monitored by a vacuum switch 132 connected to the main CPU 126. Vacuum accumulator tank 130 communicates with safety valve 128 through a check valve 133.

Helium for priming and/or charging the system is stored in tank 134. Helium pressure is monitored by main CPU 126 through helium pressure sensor 136. The helium passes through a pressure regulator 138 and flow restrictor 140 to the priming valve 142. Priming valve 142 is controlled by main CPU 26 and connects the input from blocking valve 144 to either the atmosphere or helium tank 134. A pump pressure sensor 146 informs the main CPU 126 of the pressure in the balloon pump system and a pump temperature sensor 148 (not shown on the pump) informs the main CPU 126 of the pump temperature. An actuator interlock switch 150 (not shown on the pump, but coupled to body portion 16 and front cover 14) signals the main CPU 126 whether or not the front cover 14 is attached to body portion 16 of the pump housing assembly 12.

The system can be primed with helium in three ways which, for the purpose of illustration, are defined as: (1) a full prime; (2) a short prime; and (3) a charge.

A full prime places a fresh vacuum in the vacuum accumulator tank 130, purges gas from the system, and then fills the system with helium. This can be programmed to occur when the entire system is shut down for more than a specific time interval (e.g., 60 seconds), or when vacuum switch 132 indicates that there is no vacuum left in the vacuum accumulator tank 130.

A short prime purges gas from the system to obtain a fresh charge of helium anytime a prime is required and there is a sufficient vacuum in the vacuum accumulator tank 130.

A charge provides enough helium to bring the pressure up to the proper level any time a minor pressure drop is detected and it has been less than some predetermined time interval since the last full or short prime.

The system is primed in a series of steps. In step 1, the pump is homed by first moving the blocking valve 144 to the priming valve 142 and then opening priming valve 142 to the atmosphere. The PMC 124 then moves the diaphragm assembly 24 from the home position to the assist-deflate position. The PMC 124 is then set to priming mode, and diaphragm assembly 24 is brought back to the home position.

Step 2 puts a vacuum in the vacuum accumulator tank 130. Diaphragm assembly 24 is then displaced through a full stroke corresponding to the fully inflated position to purge gas from the system, indicated by a zero reading from pressure sensor 146 (i.e., a reference pressure). Safety valve 128 is then switched to the vacuum side and diaphragm assembly 24 is translated to the home position to pull a vacuum into the system. Vacuum sufficiency can be checked by choosing a suitable threshold value to be processed by main CPU 126, for example, −350 mm Hg after one pump, −275 mm Hg after two pumps, or −250 mm Hg after three or four pumps.

If vacuum is insufficient, the safety valve 128 is again switched to the blocking valve to lock vacuum in tank 130, and pump 10, catheter 122 and balloon 120 are opened to the atmosphere and the foregoing steps to draw vacuum are repeated until a suitable vacuum is attained.

In step 3, if vacuum is sufficient, main CPU 126 can perform a vacuum leak check by monitoring the vacuum pressure for a period of, for example, 2 seconds, by averaging 100 ms of pressure samples, waiting 2 seconds, and then averaging another 100 ms of pressure samples to determine whether the latter average differs by more than a predetermined value from the former average.

After obtaining the requisite vacuum pressure in vacuum tank 130, in step 4 the pump system is then purged of gas. The safety valve 128 is switched to blocking valve 144, the blocking valve 144 is switched to the priming valve 142 and the priming valve 142 is opened to the atmosphere. Diaphragm assembly 24 is then moved to the inflate position to expel gas through the open priming valve 142. If there already is a vacuum in vacuum accumulator tank 130, then step 2 was not performed (i.e., a short prime) and the pressure sensor 146 should be verified to read zero. The blocking valve 144 is then moved to the blocking position and diaphragm assembly 24 is displaced to the home position.

If this is a short prime, step 3 is repeated to check for leaks in the system; if this is a full prime, the leak check was completed in step 3 and the system is then ready to be charged with helium.

In step 5, the system is charged with helium. First, the priming valve 142 is switched to the helium line. The blocking valve 144 is then moved to the priming valve 142 to permit helium to fill the vacuum. When the pressure sensor 146 detects a pressure rise to a predetermined value, for example, −250 mm Hg, the PMC 124 moves diaphragm assembly 24 from the priming mode deflate or home position to the assist-deflate position. Main CPU 126 monitors pressure sensor 146 until the pressure rises to within a predetermined range, for example, between −8 and −13 mm Hg. Blocking valve 144 is then moved to the blocked position, and the priming valve 142 is opened to the atmosphere. The system can then be checked for leaks in accordance with the procedures of step 3 described above. After the leak check, the system is ready to begin the circulatory assist procedure.

The present invention has been shown and described in what is considered to be the most practical and preferred embodiment. It is anticipated, however, that departures can be made therefrom and that obvious modifications will occur to persons skilled in the art.

I claim:

1. A circulatory assist device, comprising:

a shuttle gas source;

a balloon catheter having a balloon associated therewith for inflation and deflation;

a pump housing having an internally disposed pumping chamber of variable volume, said pump housing communicating with said balloon catheter and said shuttle gas source for priming said pumping chamber, said balloon catheter and said balloon with said shuttle gas;

a diaphragm assembly for varying the volume of said pumping chamber to pressurize and depressurize said shuttle gas, said diaphragm assembly including a diaphragm having an outer periphery affixed to said housing;

a reversible motor-driven actuator disposed in said housing for mechanically displacing said diaphragm assembly in a first pumping direction to decrease the volume of said pumping chamber to pressurize said shuttle gas to inflate the balloon, and in a second pumping direction to increase the volume of said pumping chamber to deflate the balloon; and a pump controller for storing a plurality of pump positions for said diaphragm assembly and for energizing said motor-driven actuator such that said motor-driven actuator displaces said diaphragm assembly between a balloon-deflate position and a balloon-inflate position at optimal time intervals for circulatory assist.

2. The balloon pump recited in claim 1, wherein said pump controller energizes said motor-driven actuator such that said motor-driven actuator variably displaces said diaphragm assembly through a range of positions between said balloon-deflate position and said balloon-inflate position to control the degree of balloon inflation.

3. The balloon pump recited in claim 1, wherein said motor-driven actuator comprises:

an elongated shaft having said diaphragm assembly attached thereto, said shaft further having a threaded exterior portion;

a planetary roller nut having an outer surface and a threaded internal portion for engaging said elongated shaft therein; and a motor for bidirectionally rotating said planetary roller nut to displace said shaft relative to said housing in said first and second pumping directions, said motor including a rotor and a stator, said rotor being coaxially disposed around and attached to said outer surface of said planetary roller nut.

4. A circulatory assist device, comprising:

a shuttle gas source;

a balloon catheter having a balloon associated therewith for inflation and deflation;

a pump housing having an internally disposed pumping chamber of variable volume, said pump housing communicating with said balloon catheter and said shuttle gas source for priming said pumping chamber, said balloon catheter and said balloon with said shuttle gas;

a diaphragm assembly for varying the volume of said pumping chamber to pressurize and depressurize said shuttle gas, said diaphragm assembly including a diaphragm having an outer periphery affixed to said housing, said diaphragm assembly further comprising a first pushing member and a second retaining member which sandwich said diaphragm;

a reversible motor-driven actuator disposed in said housing for mechanically displacing said diaphragm assembly in a first pumping direction to decrease the volume of said pumping chamber to pressurize said shuttle gas to inflate the balloon, and in a second pumping direction to increase the volume of said pumping chamber to deflate the balloon, said motor-driven actuator including an elongated shaft, said shaft having said diaphragm assembly attached thereto, said shaft further having a threaded exterior portion; a planetary roller nut having an outer surface and a threaded internal portion for engaging said threaded exterior portion of said elongated shaft therein; and a motor for bidirectionally rotating said planetary roller nut to displace said shaft relative to said housing in said first and second pumping directions, said motor including a rotor coaxially disposed around and attached to said outer surface of said planetary roller nut; and a pump controller for storing a plurality of pump positions for said diaphragm assembly and for energizing said motor-driven actuator such that said motor-drive actuator displaces said diaphragm assembly between a balloon-deflate position and a balloon-inflate position at optimal time intervals for circulatory assist.

5. A circulatory assist device, comprising:

a shuttle gas source;

a catheter having an instrument associated therewith for inflation and deflation;

a pump housing having an internally disposed pumping chamber of variable volume, said pump housing communicating with said catheter and said shuttle gas source for priming said pumping chamber, said catheter and said instrument with said shuttle gas;

a diaphragm assembly for varying the volume of said pumping chamber to pressurize and depressurize said shuttle gas, said diaphragm assembly including a diaphragm having an outer periphery affixed to said housing, said diaphragm assembly further comprising a first pushing member and a second retaining member which sandwich said diaphragm;

a reversible motor-drive actuator disposed in said housing for mechanically displacing said diaphragm assembly in a first pumping direction to decrease the volume of said pumping chamber to pressurize said shuttle gas to inflate the instrument, and in a second pumping direction to increase the volume of said pumping chamber to deflate the instrument, said motor-drive actuator including an elongated shaft having said diaphragm assembly attached thereto, said shaft further having a threaded exterior portion; a planetary roller nut having an outer surface and a threaded internal portion for engaging said threaded exterior portion of said elongated shaft therein; and a motor for bidirectionally rotating said planetary roller nut to displace said shaft relative to said housing in said first and second pumping directions, said motor including a rotor coaxially disposed around and attached to said outer surface of said planetary roller nut; and a pump controller for storing a plurality of pump positions for said diaphragm assembly and for energizing said motor-driven actuator such that said motor-drive actuator displaces said diaphragm assembly between an instrument-deflate position and a instrument-inflate position at optimal time intervals for circulatory assist.

\* \* \* \* \*